United States Patent
Volpe et al.

(10) Patent No.: US 9,454,219 B2
(45) Date of Patent: *Sep. 27, 2016

(54) SYSTEM AND METHOD FOR CONSERVING POWER IN A MEDICAL DEVICE

(71) Applicant: ZOLL MEDICAL CORPORATION, Chelmsford, MA (US)

(72) Inventors: Shane S. Volpe, Saltsburg, PA (US); Richard A. Rattanni, Verona, PA (US); Thomas E. Kaib, Irwin, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/974,794

(22) Filed: Dec. 18, 2015

(65) Prior Publication Data
US 2016/0103482 A1    Apr. 14, 2016

Related U.S. Application Data

(63) Continuation of application No. 14/531,794, filed on Nov. 3, 2014, which is a continuation of application No. 12/833,096, filed on Jul. 9, 2010, now Pat. No. 8,904,214.

(51) Int. Cl.
| | |
|---|---|
| *G06F 1/00* | (2006.01) |
| *G06F 1/32* | (2006.01) |
| *A61N 1/08* | (2006.01) |
| *A61N 1/39* | (2006.01) |
| *G06F 9/54* | (2006.01) |
| *G06F 19/00* | (2011.01) |

(52) U.S. Cl.
CPC .............. *G06F 1/3296* (2013.01); *A61N 1/08* (2013.01); *A61N 1/3925* (2013.01); *A61N 1/3975* (2013.01); *G06F 1/3203* (2013.01); *G06F 1/324* (2013.01); *G06F 1/3234* (2013.01); *G06F 9/542* (2013.01); *G06F 19/3406* (2013.01); *Y02B 60/1217* (2013.01); *Y02B 60/1285* (2013.01)

(58) Field of Classification Search
CPC .... G06F 1/3296; G06F 19/3406; G06F 1/26; G06F 1/32
See application file for complete search history.

(56) References Cited

U.S. PATENT DOCUMENTS

| | | | |
|---|---|---|---|
| 3,553,651 A | 1/1971 | Bird et al. | |
| 5,924,979 A | 7/1999 | Swedlow et al. | |
| 6,148,233 A | 11/2000 | Owen et al. | |
| 6,546,285 B1 | 4/2003 | Owen et al. | |

(Continued)

OTHER PUBLICATIONS

Herlihy et al. The Art of Multiple Processor Programming. Chapter 1, p. 1. Mar. 3, 2008.

(Continued)

*Primary Examiner* — Jaweed A Abbaszadeh
*Assistant Examiner* — Austin Hicks
(74) *Attorney, Agent, or Firm* — Finch & Maloney PLLC

(57) ABSTRACT

A system and method for conservation of battery power in a portable medical device is provided. In one example, a processor arrangement that includes a plurality of processors is implemented. At least one of these processors is configured to execute the critical functions of the medical device, while one or more other processors assume a reduced service level, thereby drawing significantly less power. According to this arrangement, the medical device conserves energy by drawing the additional electrical power needed to activate the additional processing power only when needed.

23 Claims, 7 Drawing Sheets

(56) References Cited

U.S. PATENT DOCUMENTS

| | | |
|---|---|---|
| 2005/0144043 A1 | 6/2005 | Holland et al. |
| 2008/0312709 A1* | 12/2008 | Volpe ............... A61B 5/0404 607/6 |
| 2009/0066366 A1 | 3/2009 | Solomon |
| 2009/0118808 A1 | 5/2009 | Belacazar et al. |
| 2009/0312650 A1 | 12/2009 | Maile et al. |
| 2010/0010559 A1* | 1/2010 | Zhang ............... A61N 1/3708 607/27 |
| 2010/0171611 A1 | 7/2010 | Gao et al. |

OTHER PUBLICATIONS

International Search Report and Written Opinion from corresponding International Application No. PCT/US2011/043368, dated Nov. 17, 2011.
Wikipedia, Automated external defibrillator, May 31, 2009, Wikipedia, section on Mechanism of operation.
Wikipedia, Multi-core processor, Dec. 11, 2009, http://web.archive.org/web/20091211134408/http://en.wikipedia.org/wiki/Multicore_processor#Hardware.

* cited by examiner

SYSTEM AND METHOD FOR CONSERVING POWER IN A MEDICAL DEVICE

CROSS-REFERENCE TO RELATED APPLICATIONS

This application claims the benefit under 35 U.S.C. §120 as a continuation of U.S. application Ser. No. 14/531,794, titled "SYSTEM AND METHOD FOR CONSERVING POWER IN A MEDICAL DEVICE," filed Nov. 3, 2014, which is a continuation of U.S. application Ser. No. 12/833,096, now U.S. Pat. No. 8,904,214, titled "SYSTEM AND METHOD FOR CONSERVING POWER IN A MEDICAL DEVICE," filed Jul. 9, 2010, each of which is hereby incorporated herein by reference in its entirety for all purposes.

BACKGROUND

1. Field of Invention

Aspects of the present invention relate to medical devices, and more particularly to apparatus and methods for conserving power in medical devices.

2. Discussion of Related Art

High performance portable medical devices typically require substantial computer processing power. One factor contributing to the demand for processing power is the large number of peripheral devices supported by many medical devices. These peripheral devices may include display devices such as LCD screens, memory devices such as synchronous dynamic random access memory, secure digital memory, universal sensor data memory and flash memory and interface devices such as universal serial bus, Bluetooth and Ethernet interfaces.

In addition, many portable medical devices perform sophisticated analysis of physiological data gathered from patients. In many instances, this analysis and any treatment initiated as a result of the analysis must be performed quickly, precisely and accurately as a patient's life may depend on it. The complexity and temporal requirements of these processing activities further contributes to the demand for processing power.

Portable medical devices also require that the components used to deliver functionality fit into a small footprint so that the medical device remains portable. In fact, many portable medical devices are required to be small and light enough to be worn by ambulatory patients. To meet these demands, portable medical devices conventionally conform to a design that includes only a single but powerful microprocessor.

SUMMARY OF INVENTION

Aspects and examples disclosed herein manifest an appreciation that the processing power required by portable medical devices equates to a significant load on the batteries used to power these devices. This, in turn, causes the battery runtime to decrease and the frequency with which batteries need recharging to increase. Consequently, the useful lifespan of the batteries is shortened. Additionally, other aspects and examples disclosed herein manifest an appreciation that, for some medical devices, conventional real time operating systems (RTOSs) lack the ability to execute instructions with the temporal precision required to effectively implement treatment methods.

For instance, some examples disclosed herein conserve battery power by implementing a processor architecture that includes a plurality of processors. At least one of these processors is configured to execute the critical functions of the medical device, while one or more other processors assume a reduced service state, thereby drawing significantly less power. According to this arrangement, the medical device conserves energy by drawing the additional electrical power needed to activate the additional processing power only when the additional processing power is required.

According to one example, a method for conserving electrical power in a therapeutic medical device is provided. The therapeutic medical device has a general purpose processor and a critical purpose processor. The method includes acts of instructing the general purpose processor to enter a reduced service state, detecting, on the critical purpose processor, at least one event that requires processing by the general purpose processor, instructing the general purpose processor to enter an active state and processing, on the general purpose processor, the at least one event.

In the method, the act of instructing the general purpose processor to enter the reduced service state may include an act of instructing the general purpose processor to enter a sleeping state. In addition, the act of detecting, on the critical purpose processor, the at least one event may include an act of detecting a critical event. Further, the act of processing, on the general purpose processor, the at least one event may include an act of providing an indication of the critical event to a user. Moreover, the act of processing, on the general purpose processor, the at least one event further may include an act of receiving an indication to delay treatment from the user. Additionally, the act of detecting, on the critical purpose processor, the at least one event may include an act of detecting expiration of a predetermined amount of time. Furthermore, the act of detecting, on the critical purpose processor, the at least one event may include an act of detecting that a shared memory is full, the shared memory being accessible by the general purpose processor and the critical purpose processor. Also, the act of processing, on the general purpose processor, the at least one event may include acts of reading data from the shared memory and storing the data in data storage.

The method may further include an act of entering, on the general purpose processor, another reduced service state after storing the data in the data storage. In addition, the method may further include an act of initiating treatment on the critical purpose processor.

According to another example, a therapeutic medical device is provided. The therapeutic medical device includes a shared memory, a general purpose processor coupled to the shared memory and configured to process at least one event and a critical purpose processor coupled to the shared memory and the general purpose processor. The general purpose processor is configured to instruct the general purpose processor to enter a reduced service state, detect at least one event that requires processing by the general purpose processor and instruct the general purpose processor to enter an active state, wherein the general purpose processor processes the at least one event that requires processing by the general purpose processor.

In the device, the critical purpose processor may be configured to instruct the general purpose processor to enter the reduced service state by instructing the general purpose processor to enter a sleeping state. In addition, the critical purpose processor may be configured to detect the at least one event by detecting a critical event. Further, the general purpose processor may be configured to process the at least one event by providing an indication of the critical event to a user. Moreover, the general purpose processor may be configured to process the at least one event by receiving an indication to delay treatment from the user. Additionally, the critical purpose processor may be configured to detect the at least one event by detecting expiration of a predetermined amount of time. Furthermore, the critical purpose processor may be configured to detect the at least one event by detecting that the shared memory is full.

In the device, the general purpose processor may be configured to process the at least one event by reading data from the shared memory and storing the data in data storage. In addition, the general purpose processor may be further configured to enter another reduced service state after storing the data in the data storage. Moreover, the critical purpose processor may be further configured to initiate treatment.

According to another example, another therapeutic medical device is provided. The device includes at least one physiological sensor, at least one therapy delivery device and a portable treatment controller coupled to the at least one physiological sensor and the at least one therapy delivery device. The portable treatment controller includes a shared memory, a general purpose processor coupled to the shared memory and configured to process at least one event and a critical purpose processor coupled to the shared memory and the general purpose processor. The general purpose processor is configured to instruct the general purpose processor to enter a reduced service state, detect at least one event that requires processing by the general purpose processor and instruct the general purpose processor to enter an active state, wherein the general purpose processor processes the at least one event that requires processing by the general purpose processor.

In the device, the critical purpose processor may be configured to instruct the general purpose processor to enter the reduced service state by instructing the general purpose processor to enter a sleeping state. In addition, the critical purpose processor may be configured to detect the at least one event by detecting a critical event via the at least one physiological sensor.

The device may further include a user interface coupled to the general purpose processor and the general purpose processor may be configured to process the at least one event by providing an indication of the critical event to a user via the user interface. In addition, the general purpose processor may be configured to process the at least one event by receiving an indication to delay treatment from the user via the user interface. Further, the critical purpose processor may be configured to detect the at least one event by detecting expiration of a predetermined amount of time. Moreover, the critical purpose processor is configured to detect the at least one event by detecting that the shared memory is full.

In the device, the general purpose processor may be configured to process the at least one event by reading data from the shared memory and storing the data in data storage. In addition, the general purpose processor may be further configured to enter another reduced service state after storing the data in the data storage. Moreover, the critical purpose processor may be further configured to initiate treatment via the at least one therapy delivery device. Also, the critical purpose processor may be configured to respond to information received from the at least one physiological sensor within 10 microseconds of receipt.

Still other aspects, examples, and advantages of these exemplary aspects and examples, are discussed in detail below. Moreover, it is to be understood that both the foregoing information and the following detailed description are merely illustrative examples of various aspects and examples, and are intended to provide an overview or framework for understanding the nature and character of the claimed aspects and examples. Any example disclosed herein may be combined with any other example in any manner consistent with at least one of the objects, aims, and needs disclosed herein, and references to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example. Furthermore, in the event of inconsistent usages of terms between this document and documents incorporate herein by reference, the term usage in the incorporated references is supplementary to that of this document; for irreconcilable inconsistencies, the term usage in this document controls.

BRIEF DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of the invention. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. In the figures:

DETAILED DESCRIPTION

Figure 1:
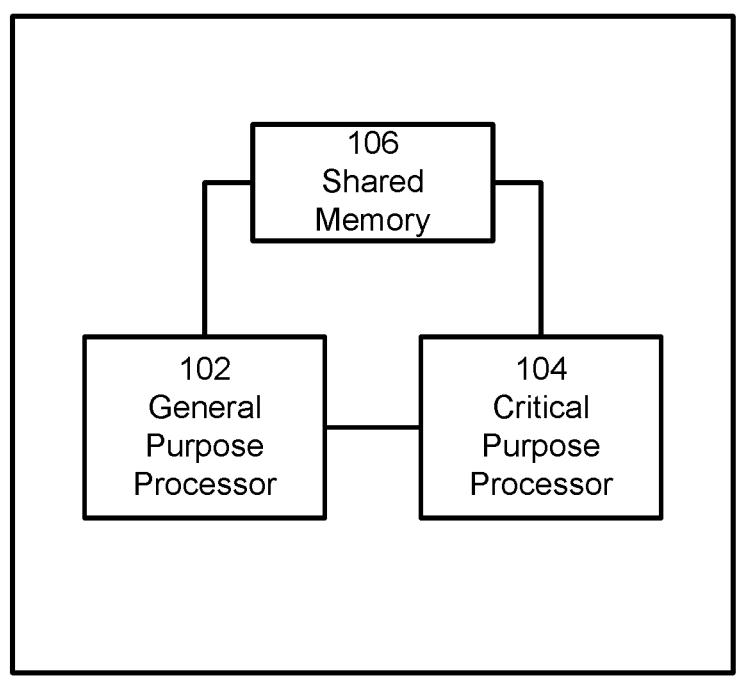
FIG. 1 is a functional block diagram of one example of a power conserving processor arrangement.

Aspects and examples relate to apparatus and processes for selectively executing instructions on particular processors within a processor arrangement. The manner in which the instructions are executed conserves electrical energy and isolates particular functionality to particular components. For instance, methods and apparatus in accord with some examples include a medical device having a critical purpose processor that is configured to execute one or more critical functions and a general purpose processor that is configured to execute the remainder of the functions of the medical device. In these examples, the critical purpose processor generally remains active while the general purpose processor generally remains inactive. This arrangement of processors results in lower power consumption by the medical device than would an arrangement including only the general purpose processor. Lower power consumption, in turn, results in decreased operating temperature which extends the life and reliability of the medical device.

In addition, this arrangement of processors isolates execution of the critical functions to a particular set of components. In this way, the processor arrangement protects the ability of the medical device to reliably, precisely and effectively execute its critical functions without interference or instability caused by execution of or change to the non-critical functions of the device. Moreover, by including a general purpose processor that executes an RTOS, this arrangement provides a rich computing platform with standard system services such as file system management and communications for the remainder of the functions of the medical device.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Power Conserving Processor Arrangement

Various examples disclosed herein conserve electrical power by harnessing multiple processors that use differing amounts of power during operation. FIG. 1 illustrates a power conserving processor arrangement 100 that is specially configured to utilize less power than a conventional, comparable single processor architecture while providing at least the same level of processing functionality as the single processor architecture. The power conserving processor arrangement 100 includes a general purpose processor 102, a critical purpose processor 104 and shared memory 106. As shown, each of these components is coupled to the other two. Both of the processors 102 and 104 can perform a series of instructions that result in manipulated data which can be stored in and retrieved from the shared memory 106. In addition, the critical purpose processor 104 can actively operate using less electrical power than the general purpose processor 102. By taking advantage of this feature, the power conserving processor arrangement 100 saves energy by employing the critical purpose processor 104 to execute instructions that would normally be executed on the general purpose processor 102 under a conventional design.

Some exemplary devices also employ the power conserving processor arrangement 100 to isolate execution of functions that are critical to the purpose of the device. In these exemplary devices, critical functions are performed by the critical purpose processor 104. Critical functions are a well defined set of limited or essential functions that the medical device employing the power conserving processor arrangement 100 is designed to provide. Particular examples of critical functions are discussed in further detail below. In addition, according to these examples, non-critical functions are performed by the general purpose processor 102. This segmentation of instruction execution provides several benefits which are discussed further below.

According to some examples, the general purpose processor 102 is configurable to operate in one of a plurality of service states that each consume differing, predetermined levels of electrical power. Moreover, in these examples, the general purpose processor 102 is configured to operate at a predefined performance level within each service state. The particular number of service states and the characteristics of the level of performance associated with each service state vary by the manufacturer or model of the processor. However, many processors conform to electrical power management standards such as the "Advanced Configuration and Power Interface Specification," (ACPI) Revision 4.0a which was published at www.acpi.info on Apr. 5, 2010. The ACPI defines processor service states and the characteristics of the level of performance associated with these service states. For example, processors complying with the ACPI may assume various power, performance and throttling states. Each of these states is associated with an amount of electrical power required to support the service state and a guaranteed level of processor performance. The aspects of processor performance that may be manipulated by various service states include, among others, the clock rate of the processor and the latency time required for the processor to assume a different service state.

In some examples, the service states that the general purpose processor 102 can assume include an active service state or one of several reduced service states. While operating in the active service state, the general purpose processor 102 can operate at or near peak performance. Thus, while in the active service state, the general purpose processor 102 can execute instructions at, or near, the maximum clock rate, maintain coherent processor caches and shift into other service states with minimal, or near minimal, latency. An example of an active service state includes the C0 power state, as defined in ACPI, when combined with a P0 performance state and with or without throttling.

When operating in reduced service states, the general purpose processor 102 operates at less than peak performance Examples of reduced service states include the C0 power state, when combined with a performance state other than P0, and any of the processor sleeping states, such as the C1 and C2 power states. The processor functionality available under these service states varies according the particular reduced service state assumed.

For example, when the general purpose processor 102 is placed in a C0 state combined with a non-P0 state, the general purpose processor 102 can execute instructions and maintain cache coherency but does so at a rate less than the maximum clock rate. Also, when the general purpose processor 102 is placed in a processor sleeping state, the general purpose processor 102 cannot execute instructions and the processor caches are flushed and invalidated. In addition, while operating in a processor sleeping state, the general purpose processor 102 may (depending on the particular processor sleeping state) require more latency time to shift into another service state. However, when in these states, the general purpose processor 102 consumes less electrical power than when in an active service state.

According to some examples, the critical purpose processor 104 is also configurable to operate in a variety of service states. These service states include at least one service state that enables the critical purpose processor 104 to execute instructions using significantly less power than would the general purpose processor 102. In addition, these service states include at least one service state that provides a performance level required for the critical purpose processor 104 to carry out a set of critical functions. In some of these examples, the critical functions have strict timing requirements that are better met by a dedicated execution environment, such as the execution environment provided by the critical purpose processor 104. For instance, some critical functions may require low jitter and response times ranging from approximately 10 milliseconds down to and including less than approximately 10 microseconds. According to these examples, the critical purpose processor 104, by executing the critical functions, allows the general purpose processor 102 to execute processes with less stringent requirements.

In some examples, the general purpose processor 102 is configured to provide an interface through which the general purpose processor 102 can receive, process and respond to service requests. These service requests may include information indicating the source of the request, the requested functions to be performed, service states to be assumed and maximum durations of active processing activity. According to these examples, the general purpose processor 102 is configured take a variety of actions in response to a service request. These actions may include verifying the source of the request, and upon proper verification of the source, assuming the requested service state, performing the requested functions and entering a reduced service state upon reaching the specified maximum duration of active execution or upon expiration of a predetermined time period.

Also, according to these examples, the critical purpose processor 104 includes a power management component that is configured to issue a service request to the general purpose processor 102 when the critical purpose processor 104 encounters an event. Events that cause the power management component to issue a service request may include any event that requires processing by the general purpose processor 102. More specifically, in some of these examples, the power management component is configured to issue a service request upon detection that the shared memory 106 is full, that a critical event has occurred or that a predetermined period of time since the general purpose processor 102 was active has transpired. A critical event may include any event related to execution of critical functionality.

In addition, in some examples, the predetermined period of time is configurable. More particularly, in at least one of these examples, the power management component is configured to issue service requests that cause the general purpose processor 102 to activate every 5 minutes and stay active for a duration of 5 seconds. In other examples, the power management component is configured for execution on a separate programmable logic device (PLD) rather than on the critical purpose processor 104.

Also, some examples implement a watchdog component that monitors the operations of the general purpose processor 102 and the critical purpose processor 104. According to these examples, while both processors are operating normally, each processor transmits a special message (referred to as a "heartbeat message") to the watchdog component at a predetermined interval specific to the processor. For instance, the predetermined interval at which the general purpose processor 102 transmits messages to the watchdog component may be 5 minutes, while the predetermined interval at which the critical purpose processor 104 transmits messages may be 1 second. If the watchdog component does not receive the messages according to the predetermined intervals, the watchdog component resets the device. In at least some examples, the watchdog component is implemented as a software process on a PLD that is separate from the general purpose processor 102 and the critical purpose processor 104.

Further, in some examples, the length of the predetermined interval is configurable or depends on previous detection of a critical event. In at least one example, the predetermined interval associated with the general purpose processor 102 is 5 minutes unless a critical event has been detected. In that instance, however, the critical purpose processor 104 temporarily sets the predetermined interval associated with the general purpose processor 102 to 5 seconds to decrease any potential latency associated with the general purpose processor 102 and the device overall. Further, in these examples, after performing any processing associated with the critical event, the general purpose processor 102 sets the predetermined interval associated with itself back to 5 minutes prior to entering a reduced service state.

According to a variety of examples, the processors 102 and 104 are commercially available processors such as processors manufactured by Texas Instruments, Intel, AMD, Sun, IBM, Motorola, Freescale and ARM Holdings. However, the processors 102 and 104 may be any type of processor, multiprocessor or controller, whether commercially available or specially manufactured. In some examples, the critical purpose processor 104 is a digital signal processor, a field-programmable gate array or a PLD. In at least one particular example, the general purpose processor 102 is an Intel® PXA270 and the critical purpose processor 104 is a Freescale™ DSP56311.

In addition, in several examples the general purpose processor 102 is configured to execute a conventional RTOS, such as RTLinux. In these examples, the RTOS may provide platform services to application software. These platform services may include inter-process and network communication, file system management and standard database manipulation. However, one of many operating systems may be used, and examples are not limited to any particular operating system or operating system characteristic. For instance, in some examples, the general purpose processor 102 may be configured to execute a non real time operating system, such as BSD or GNU/Linux.

In the example illustrated in FIG. 1, the shared memory 106 is configured to store data during operation of the power conserving processor arrangement 100. In some examples, the shared memory 106 includes a relatively high performance, volatile, random access memory such as dynamic random access memory (DRAM), static memory (SRAM) or synchronous DRAM. However, the shared memory 106 may include any device for storing data, such as a non-volatile memory, with sufficient throughput and storage capacity to support the functions described herein. In the example of FIG. 1, the shared memory 106 has a storage capacity of 1 megabyte and is coupled to both processors 102 and 104. Thus, in some examples, the shared memory 106 may include hardware or software configured to enable concurrent access to stored data. In at least one example, the shared memory 106 includes dual port RAM. While in other examples, the shared memory 106 includes a PLD coupled to a single port synchronous DRAM. In these examples, the PLD provides an interface that services concurrent memory requests from the processors 102 and 104.

According to some examples, the general purpose processor 102 swaps between a critical purpose operating system and a general purpose operating system and exploits differences between the operating power requirements of each operating system to conserve power used by the device. In these examples, each of the operating systems operates a subset of the overall peripherals available to the general purpose processor 102. The particular peripherals operated by either operating system are based on the functionality executed within each operating system. Thus, the critical purpose operating system may operate different peripherals than the general purpose operating system. Examples of these peripherals include any hardware that interacts with a processor. Thus, exemplary peripherals include memory, UARTs, display controllers, audio controllers, USB controllers and wireless or wired network interface controllers, among others.

Also, according to these examples, a device including the general purpose processor 102 configured to swap operating systems conserves power because while either operating system is running, a power management component places the peripherals that are operated by the dormant operating system into a reduced service state. The particular service state into which the power management component places each peripheral depends on the sophistication of each peripheral. For instance, in some examples, the power management component can simply discontinue supply of power to peripherals with insufficient power state management functionality to be managed in another way, such as some types of memory. While in other examples, the power management component can issue commands to enter reduced service states to peripherals exposing power state management interfaces, such as certain models of UARTs.

Figure 2:
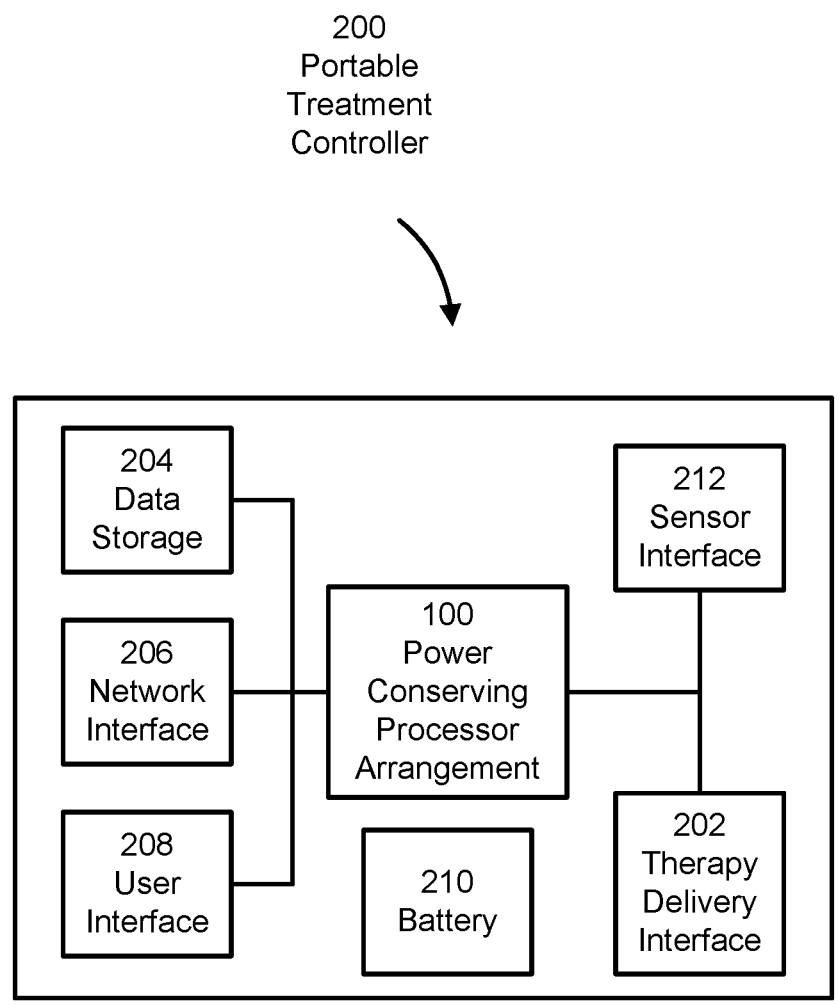
FIG. 2 is a functional block diagram of one example of a portable treatment controller.
Figure 3:
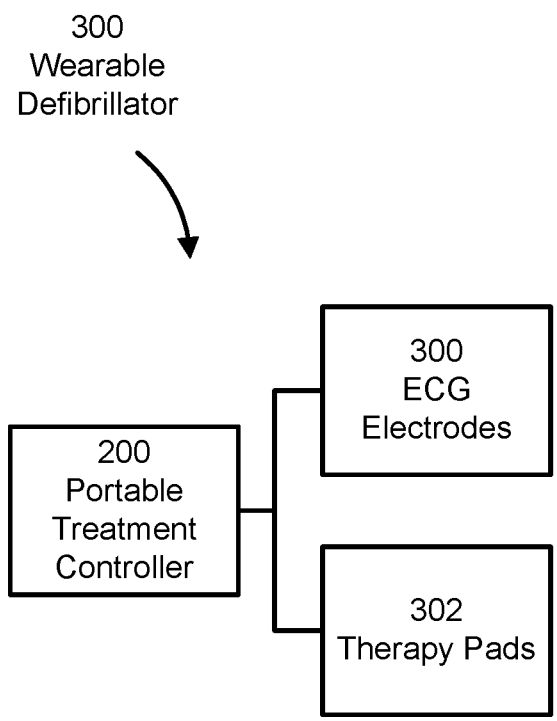
FIG. 3 is a functional block diagram of one example of a wearable defibrillator.

The power conserving processor arrangement 100 has a variety of potential applications and is well suited to devices that must perform a critical set of functions in an environment with scarce resources. Examples of such devices include critical care medical devices, such as a wearable external defibrillator. The power conserving processor arrangement 100 may also be leveraged to isolate particular components of a device when it is advantageous to do so, for example, to allow government regulated components of a device to remain unchanged while introducing new functionality to a device via other components. FIG. 2 and FIG. 3 illustrate examples of devices that utilize the power conserving processor arrangement 100. In addition, the power conserving processor arrangement 100 may be included within a wearable medical treatment device as described in commonly owned U.S. patent application Ser. No. 12/833,173 entitled "Wearable Medical Treatment Device," filed on Jul. 9, 2010, which is incorporated by reference herein in its entirety.

Portable Treatment Controller

FIG. 2 illustrates a portable treatment controller 200 that is configured to perform the critical functions of monitoring physiological information for abnormalities and initiating treatment of detected abnormalities. As shown, the portable treatment controller 200 includes the power conserving processor arrangement 100, a sensor interface 212, a therapy delivery interface 202, data storage 204, a communication network interface 206, a user interface 208 and a battery 210. In this illustrated example, the battery 210 is a rechargeable 3 cell 2200 mAh lithium ion battery pack that provides electrical power to the other device components with a minimum 24 hour runtime between charges. The sensor interface 212 and the therapy delivery interface 202 are coupled to the power conserving processor arrangement 100 and more particularly to the critical purpose processor 104. The sensor interface 212 and the therapy delivery interface 202 are coupled to the critical purpose processor 104 and the critical purpose processor 104 is configured to perform the critical functions of the portable treatment controller 200 using interfaces 202 and 212. As is discussed further below, in some examples these functions include functions requiring a real time processing. For instance, within the context of a wearable defibrillator such as the wearable defibrillator discussed below with regard to FIG. 3 below, these critical functions may include charging the capacitors to a particular voltage, digital sampling and analysis of ECG information and generation of the delivered energy waveform.

Analogously, the data storage 204, the network interface 206 and the user interface 208 are also coupled to the power conserving processor arrangement 100, and more particularly to the general purpose processor 102, and the general purpose processor 102 is configured to perform the non-critical functions using these components. In some examples, these non-critical functions include functions that do not require real time processing. Under the design illustrated in FIG. 2, the portable treatment controller 200 can perform both critical and non-critical functions while consuming less energy than a conventional, single processor device having the same functionality. In addition, the portable treatment controller 200 shown in FIG. 2 prevents disruption of critical functions from hardware and software faults that may occur during execution of non-critical functions.

In the example shown, the data storage 204 includes a computer readable and writeable nonvolatile data storage medium configured to store non-transitory instructions and other data. The instructions may include executable programs or other code that can be executed by either the general purpose processor 102 or the critical purpose processor 104. The data storage 204 also may include information that is recorded, on or in, the medium, and this information may be processed by the processor 102 or 104 during execution of instructions. More specifically, the information may be stored in one or more data structures specifically configured to conserve storage space or increase data exchange performance. The instructions may be persistently stored as encoded signals, and the instructions may cause the processors 102 or 104 to perform any of the functions described herein. The medium may, for example, be optical disk, magnetic disk or flash memory, among others and may be permanently affixed to, or removable from, the portable treatment controller 200.

According to several examples, the general purpose processors 102 is configured to cause data to be read from the nonvolatile recording medium into another memory, such as the shared memory 106 described above with reference to FIG. 1, that allows for access to the data by either of the processors 102 or 104. The processors 102 or 104 can manipulate the data within the shared memory 106, and the general purpose processor 102 can copy the data to the storage medium associated with the data storage 204 after processing is completed. A variety of components may manage data movement between the data storage 204 and the shared memory 106 and examples are not limited to particular data management components. Further, examples are not limited to a particular memory, memory system or data storage system.

As shown in FIG. 2, the portable treatment controller 200 includes several system interface components 202, 206 and 212. Each of these system interface components is configured to exchange, i.e. send or receive, data with specialized devices that may be located within the portable treatment controller 200 or elsewhere. The components used by the interfaces 202, 206 and 212 may include hardware components, software components or a combination of both. In the instance of each interface, these components physically and logically couple the portable treatment controller 200 to one or more specialized devices. This physical and logical coupling enables the portable treatment controller 200 to both communicate with and, in some instances, control the operation of specialized devices. As discussed further below, these specialized devices may include physiological sensors, therapy delivery devices and computer networking devices.

According to various examples, the hardware and software components of the interfaces 202, 206 and 212 employ a variety of coupling and communication techniques. In some examples, the interfaces 202, 206 and 212 use leads, cables or other wired connectors as conduits to exchange data between the portable treatment controller 200 and specialized devices. In other examples, the interfaces 202, 206 and 212 communicate with specialized devices using wireless technologies to such as radio frequency or infrared technology. The software components included in the interfaces 202, 206 and 212 enable the power conserving processor arrangement 100 to communicate with specialized devices. These software components may include elements such as objects, executable code and populated data structures. Together, these software components provide software interfaces through which the power conserving processor arrangement 100 can exchange information with specialized devices. Moreover, in at least some examples where one or more specialized devices communicate using analog signals, the interfaces 202, 206 and 212 further include components configured to convert analog information into digital information, and visa-versa, to enable the power conserving processor arrangement 100 to communicate with specialized devices.

As discussed above, the system interface components 202, 206 and 212 shown in the example of FIG. 2 support different types of specialized devices. For instance, the components of the sensor interface 212 couple the power conserving processor arrangement 100, and, in some examples, the critical purpose processor 104, to one or more physiological sensors such as a body temperatures sensors, respiration monitors and dry capacitive electrocardiographic (ECG) electrodes. Additionally, in some examples, the components of the sensor interface 212 couple the general purpose processor 102 to one or more physiological sensors. In these examples, the one or more physiological sensors may include sensors with a relatively low sampling rate, such as wireless sensors.

In some examples, the sensor interface 212 includes a falloff detection component configured to sense a lack of proper coupling between these physiological sensors and a patient. In these examples, the critical purpose processor 104 is configured to record this critical event in the shared memory 106 and issue a service request to the general purpose processor 102. Further, in these examples, the general purpose processor 102 is configured to notify a user of the decoupled sensor via the user interface 208.

The components of the therapy delivery interface 202 couple one or more therapy delivery devices, such as capacitors and defibrillator electrodes, to the critical purpose processor 104. In addition, the components of the network interface 206 couple the general purpose processor 102 to a computer network via a networking device, such as a bridge, router or hub. According to a variety of examples, the network interface 206 supports a variety of standards and protocols, examples of which include USB, TCP/IP, Ethernet, Wireless Ethernet, Bluetooth, ZigBee, M-Bus, IP, IPV6, UDP, DTN, HTTP, FTP, SNMP, CDMA, NMEA and GSM. To ensure data transfer is secure, in some examples, the portable treatment controller 200 can transmit data via the network interface 206 using a variety of security measures including, for example, TSL, SSL or VPN. In other examples, the network interface 206 includes both a physical interface configured for wireless communication and a physical interface configured for wired communication.

Thus, the various system interfaces incorporated in the portable treatment controller 200 allow the device to interoperate with a wide variety of devices in various contexts. For instance, some examples of the portable treatment controller 200 are configured to perform a process of sending critical events and data to a centralized server via the network interface 206. An illustration of a process in accord with these examples is disclosed in U.S. Pat. No. 6,681,003, entitled "DATA COLLECTION AND SYSTEM MANAGEMENT FOR PATIENT-WORN MEDICAL DEVICES" and issued on Jan. 20, 2004 which is hereby incorporated by reference in its entirety.

The user interface 208 shown in FIG. 2 includes a combination of hardware and software components that allow the portable treatment controller 200 to communicate with an external entity, such as a user. These components are configured to receive information from actions such as physical movement, verbal intonation or thought processes. In addition, the components of the user interface 208 can provide information to external entities. Examples of the components that may be employed within the user interface 208 include keyboards, mouse devices, trackballs, microphones, electrodes, touch screens, printing devices, display screens and speakers.

In some examples, the portable treatment controller 200 includes additional components configured to enable the portable treatment controller 200 to recover from operational failure. For instance, as discussed above according to one example, the portable treatment controller 200 includes a watchdog component configured to perform a restart of the portable treatment controller 200. In this example, either the general purpose processor 102 or the critical purpose processor 104 can force a restart of the portable treatment controller 200 via the watchdog component, should either processor encounter an unrecoverable hardware or software fault.

The particular abnormalities treatable by the portable treatment controller 200 vary based on the type of physiological information collected via the sensor interface 212 and the therapies that can be initiated via the therapy delivery interface 202. For instance, according to some examples, the sensor interface 212 includes components configured to receive ECG data. Also, in these examples, the therapy delivery interface 202 includes components configured to deliver a therapeutic shock to the heart of a patient in the event that the ECG data indicates a cardiac dysrhythmia. A particular example of the portable treatment controller 200 that is included in a wearable defibrillator is discussed below with reference to FIG. 3.

Wearable Defibrillator

FIG. 3 is a functional block diagram of a wearable defibrillator 300 that is configured to implement the critical functions of monitoring an ambulatory patient's ECG information and, when needed, administering a therapeutic shock to the patient. Such a wearable defibrillator is ideally suited to take advantage of the unique capabilities afforded by the portable treatment controller 200. For example, wearable defibrillators, such as the LifeVest® wearable defibrillator available from ZOLL® Corporation, are typically worn nearly continuously for two to three months at a time. During the period of time in which they are worn, the wearable defibrillator needs to continuously monitor the vital signs of the patient, to be user friendly and accessible, to be as light-weight, comfortable, and portable as possible, and to be capable of delivering one or more life-saving therapeutic shocks when needed. Given the substantial amount of power that needs to be delivered during each therapeutic shock, it is imperative that power consumption during normal patient monitoring and operation be reduced to an absolute minimum.

As illustrated, the wearable defibrillator 300 includes the portable treatment controller 200, ECG electrodes 300 and therapy pads 302. The ECG electrodes 300 are coupled to the portable treatment controller, and more particularly to the critical purpose processor 104, via the sensor interface 212. Similarly, the therapy pads 302 are coupled to the portable treatment controller 200, and more specifically to the critical purpose processor 104, via the therapy delivery interface 202.

When utilized in the example of the wearable defibrillator 300, the components of the portable treatment controller 200 are further configured to support the critical functions of the wearable defibrillator 300. More specifically, according to this example, the battery 210 has sufficient capacity to administer one or more therapeutic shocks and the therapy delivery interface 202 has wiring suitable to carry the load to the therapeutic electrodes. Moreover, in the example shown, the battery 210 has sufficient capacity to deliver up to 5 or more therapeutic shocks, even at battery runtime expiration. As previously noted, the power delivered by a therapeutic shock of the wearable defibrillator 300 is substantial, for example approximately 150 Joules. Despite the large amount of power needed to deliver a therapeutic shock and the small footprint of the device itself, the wearable defibrillator 300 can charge capacitors within 20 seconds, notify the patient that a therapeutic shock is imminent, wait for a period (e.g. 25 seconds) to allow a patient to prevent treatment, and if appropriate, deliver the therapeutic shock within total elapsed time of 40 to 45 seconds from detection of a condition treatment without disruption to its data processing and analysis capabilities. This quick charge capability is important because the efficacy of the therapeutic shock decreases significantly when delivered over 1 minute after indication of an abnormal rhythm that should be treated with a therapeutic shock.

Continuing this example, the critical purpose processor 104 is configured to receive ECG information from the ECG electrodes 300, detect abnormal heart rhythms based on the information received from the ECG electrodes 300, charge capacitors coupled to the therapy pads 302 and administer a therapeutic shock to the patient, unless a user intervenes within a predetermined period of time via the user interface 208. In at least one example, the predetermined period of time in which a user may intervene does not end until actual delivery of the therapeutic shock. An example of the methods used to detect abnormal heart rhythms can be found in U.S. Pat. No. 5,944,669, entitled "APPARATUS AND METHOD FOR SENSING CARDIAC FUNCTION" and issued on Aug. 31, 1999 which is hereby incorporated by reference in its entirety. Additionally, an example of the general features of a wearable defibrillator can be found in U.S. Pat. No. 6,280,461, entitled "PATIENT-WORN ENERGY DELIVERY APPARATUS" and issued on Aug. 28, 2001 which is hereby incorporated by reference in its entirety.

In another example of the wearable defibrillator 300, the general purpose processor 102 is configured to perform several non-critical functions. These non-critical functions may leverage the robust computing platform provided by the general purpose processor 102 (in combination with an RTOS) without disrupting the critical functions of the device. Some examples of these non-critical functions include notifying emergency personnel of the location of a patient who just received a therapeutic shock via the network interface 206, providing users of the device with the historical physiological data of the wearer of the device via the user interface 208 and notifying the device manufacturer of potential performance issues within the device that may require repair to or replacement of the device via the network interface 206. Moreover, these non-critical functions include maintaining a history of data and events by storing this information in the data storage 204, communicating with the user via the user interface 208 and reporting data and events via the network interface 206. Example processes used to conserve energy while processing critical events and maintaining the history of critical data are discussed further below with regard to FIGS. 4, 5 and 6. In addition, other non-critical functions may perform additional operations on the history of critical data. For instance, in one example, a non-critical function analyzes the history of critical data to predict worsening heart failure or an increased risk of sudden cardiac death.

In other examples, a wearable defibrillator includes additional devices, features and functions that, when integrated with the computing platform based on the power conserving processor arrangement 100, allow the wearable defibrillator to adapt, over extended periods of time, to the individual needs of each patient. One such example is disclosed with reference FIG. 1 of co-pending U.S. patent application Ser. No. 12/002,469, entitled "WEARABLE MEDICAL TREATMENT DEVICE WITH MOTION/POSITION DETECTION" and filed on Dec. 17, 2007 which is hereby incorporated by reference in its entirety. This example includes additional sensors, such as motion sensors, to provide additional functionality and is illustrated herein with reference to FIG. 3A.

Figure 3A:
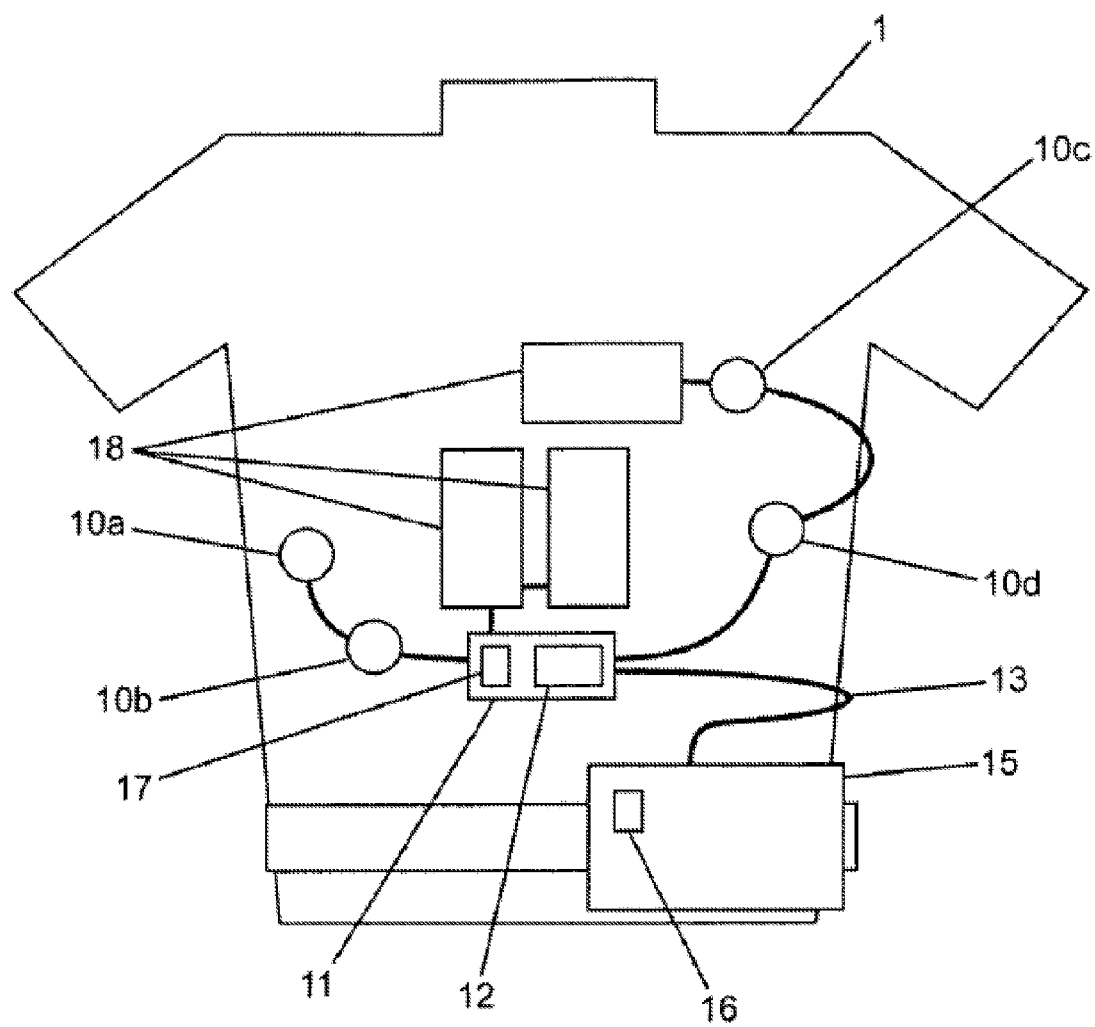
FIG. 3A is a schematic block diagram of one example of a wearable defibrillator.

FIG. 3A shows a patient 1 with a wearable defibrillator. Typically the wearable defibrillator shown would be worn as a vest, belt and/or other clothing In this example, four sensing electrodes 10a, b, c, d, or physiological sensors are shown. These sensors are positioned adjacent to the body of patient and in proximity to the skin of the patient. While this example includes four cardiac sensing electrodes and is for cardiac monitoring and treatment, other medical functions could also be appropriately monitored or treated. In this example, a node, 11, is used and the sensors 10a, b, c, d and treatment devices 18 connect to the node. In this example, node 11 electrically couples the sensors 10a, 10b, 10c and 10d, and therapy pads or treatment devices 18 to a portable treatment controller in accord with the portable treatment controller 200 described above. The node 11 could be on the belt or on other patient locations. The therapy pads or treatment devices 18 provide treatment when a sensed condition indicates the desirability of a treatment. In some examples, the treatment devices 18 include an impedance reducing substance, such as an impedance reducing gel, that is automatically applied by the treatment device 18 prior to issuing a therapeutic shock to the patient.

This example of a wearable defibrillator also includes motion sensors. While various examples may use any motion sensor, in the present example, accelerometers are used. Such sensors indicate accelerating movements. Because of the nature of human movements, generally comprising short distance and short duration, accelerometers give a very acceptable indication of patient movement. Single axis accelerometers can be used as well as multi-axis sensors.

In this example, two accelerometers 16, 17 are used. One accelerometer 17 is located on the node 11 and a second 16 is used on the monitor 15 that includes the portable treatment controller 200. It is understood that some examples use a single accelerometer or position/force/motion detector, and still other examples may use three or more. Using multiple sensors permits the power conserving processor arrangement 100 to implement a treatment method that evaluates accelerometer (sensor) differentials and predicts patient activity and accelerometer reliability. The use of multiple accelerometers permits separate and independent evaluation of patient movements from multiple perspectives which, in turn, enables a multiple perspective comparison of the movements to best determine patient activity and equipment function. In addition, the use of multiple accelerometers, as opposed to a single accelerometer, allows the treatment method to better filter noise generated from patient motion or biological signals such as muscle noise. The actual treatment method used may depend upon the characteristics of the patient, the diagnostic requirement of each individual doctor, and the condition(s) he wishes to monitor. Any or all of the activities determined by the wearable defibrillator may be used for these functions. In addition, the accelerometers can be combined with other inputs, for example, to determine if one or more of the sensors 10*a*, 10*b*, 10*c* or 10*d* is no longer in intimate contact with the patient.

Additionally, the treatment method executed by the power conserving processor arrangement 100 may accelerate or delay treatment. For instance, in some examples, the critical purpose processor 104 is configured to, upon detecting an abnormal condition, request that the general purpose processor 102 determine if the default treatment timeline should be adjusted. According to one example, the general purpose processor 102 is configured to make this determination by stimulating the patient, monitoring the patient for a response to the stimulus and adjusting the default treatment timeline based on the nature of the response received (or the lack thereof). In this example, the monitor 15 is configured to provide the stimulus via the user interface 208 or the therapy device interface 202. The stimulus may be any stimulus perceptible by the patient. Examples of stimuli that the monitor 15 may produce include visual (via a display included in the monitor 15), audio (via a speaker included in the monitor 15), tactile stimulation (via a vibrator device included in the node 11) or mild stimulating alarm shock (via the treatment devices 18).

Continuing this example, the general purpose processor 102 is configured to respond to the request for adjustment of the treatment timeline upon receipt and processing of a patient response. Patient responses may include any response that the monitor 15 is configured to process. Example responses include tactile responses (via a button, touch screen or other tactilely activated user interface element in the monitor 15), vocal responses (via a microphone in the monitor 15) and motion based responses (via the accelerometers 16 and 17).

In various examples, the general purpose processor 102 is configured to determine the type of adjustment to the treatment timeline and the magnitude of the adjustment based on the treatment urgency and patient readiness indicated in the patient response. For instance, in one example, the general purpose processor 102 is configured to respond with a decreased treatment timeline when the accelerometers 16 and 17 detect little or no motion from the patient in response to the stimulus. Alternatively, in this example, the general purpose processor 102 is also configured to delay treatment (increase the treatment timeline), or completely cancel treatment, when directed to do so by a user via the user interface 208. Thus, the general purpose processor 102 provides sophisticated user interface and patient monitoring functionality without impact to the critical purpose functions implemented using the critical purpose processor 104.

In other examples, the monitor 15 that includes the portable treatment controller 200 has a data storage 204 that is sized to store months or years of sensor information, such as ECG data, that is gathered over several monitoring and treatment periods. These monitoring and treatment periods may include continuous monitoring periods of approximately 23 hours (and substantially continuous monitoring periods of approximately 1-2 months) during which several treatments may be delivered to the patient. In some of these examples, the general purpose processor 102 is configured to analyze the stored sensor information and to determine adjustments to the treatment method, or alternative treatment methods, of benefit to the patient. For instance, in one example, the general purpose processor 102 is configured to analyze ECG data collected substantially contemporaneously with each instance of patient initiated delay, or cancellation, of treatment. In this example, the general purpose processor 102 is configured to analyze the stored months of ECG data to recognize individualized, idiosyncratic rhythms that, while not normal, do not indicate a need for treatment. In some examples, the portable treatment controller 200 may automatically adjust its treatment method to better suit the patient by not initiating treatment in response to the recognized, idiosyncratic rhythm This adjustment may be performed in conjunction with review by appropriate medical personnel.

Thus, examples in accord with FIG. 3A provide for a wearable defibrillator that collects and stores substantial amounts of historical ECG information and that tailors its treatment method based on the stored information to provide superior patient care. In addition, the wearable defibrillator shown in FIG. 3A can be used in a variety of patient care scenarios where a conventional implantable cardioverter-defibrillator cannot. Examples of these scenarios include treatment when the patient is awaiting a pending transplant or where the patient has a systemic infection (e.g. influenza or osteomyelitis), myocarditis, intra-ventricular thrombus, cancer or a life-limiting serious illness such that an implantable device is not medically prudent.

In various examples disclosed herein, components read parameters that affect the functions performed by the components. For instance, in at least one example, the general purpose processor 102 is configured to read a parameter defining a particular reduced service state to assume after initialization. These parameters may be physically stored in any form of suitable memory including volatile memory (such as RAM) or nonvolatile memory (such as flash memory). In addition, the parameters may be logically stored in a propriety data structure (such as a database or file defined by a user mode application) or in a commonly shared data structure (such as an application registry that is defined by an operating system). In addition, some examples provide for both system and user interfaces that allow external entities to modify the parameters and thereby configure the behavior of the components.

In summary, examples disclosed herein provide for a processor architecture that provides a host of advantages when used in the context of a portable medical device. These advantages include enabling the portable medical device to provide advanced functionality while conserving electrical power, thereby increasing battery runtime and extending the useful life of the portable medical device. Other advantages include the ability to continuously monitor and store patient data over a prolonged duration without compromising the ability of the device to provide therapy when needed. In addition, the processor arrangement disclosed herein allows manufacturers of medical devices to isolate the components of the medical device that deliver critical functions involving patient care. This isolation promotes safe and reliable execution and allows new functions, which might otherwise destabilize the critical functionality, to be implemented using other components. Likewise, isolation of regulated functionality allows medical devices employing the processor arrangement disclosed herein introduce new features and functions without destabilizing components already approved by governmental agencies such as the FDA.

Energy Conserving Processes

Figure 4:
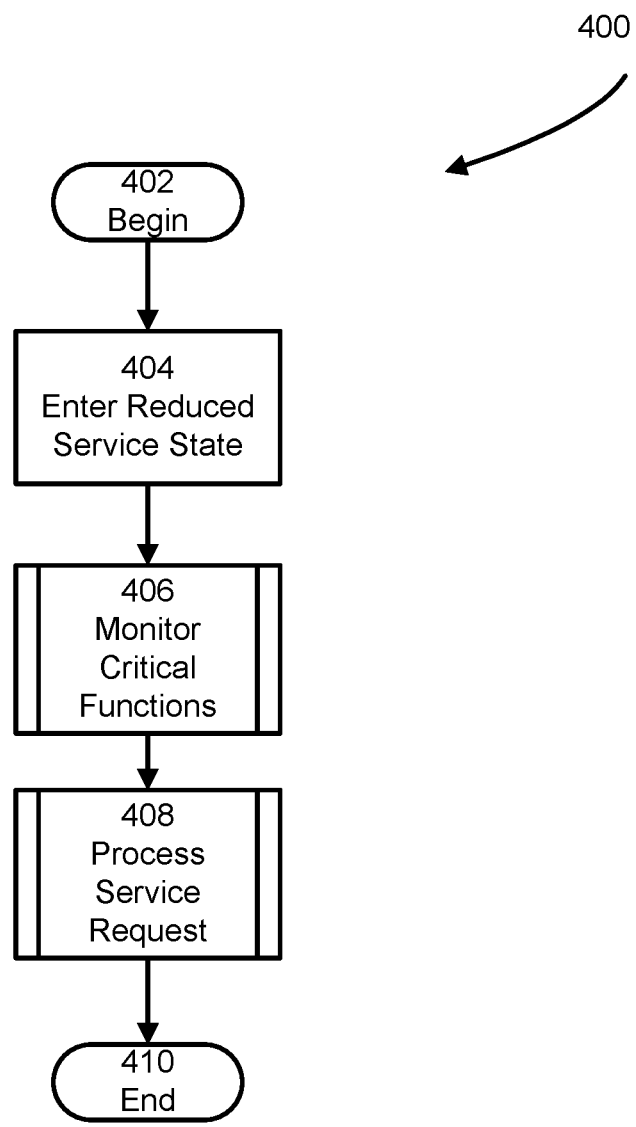
FIG. 4 is a flow diagram of one example of a method for conserving power used by a medical device using a processor arrangement.

Various examples provide processes through which a medical device conserves electrical energy while processing events and maintaining a history of data and events. In these examples, the medical device is arranged to include the power conserving processor arrangement 100 and specially configured to perform the functions disclosed herein. FIG. 4 illustrates one such process 400 that includes acts of entering a reduced service state, monitoring critical functions and processing events. Process 400 begins at 402.

In act 404, the medical device enters a reduced service state. According to some examples, the general purpose processor 102 enters the reduced service state upon determining that there are no unprocessed requests to act upon. This reduced service state is configurable and may include one or more processor performance or sleeping states.

In act 406, the medical device monitors critical functions. According to a variety of examples, the critical purpose processor 104 monitors the critical functions of the medical device. Acts in accord with these examples are discussed below with reference to FIG. 5.

In act 408, the medical device processes a service request. According to a various examples, the critical purpose processor 104 causes the general purpose processor 102 to process the service request. Acts in accord with these examples are discussed below with reference to FIG. 6.

Figure 5:
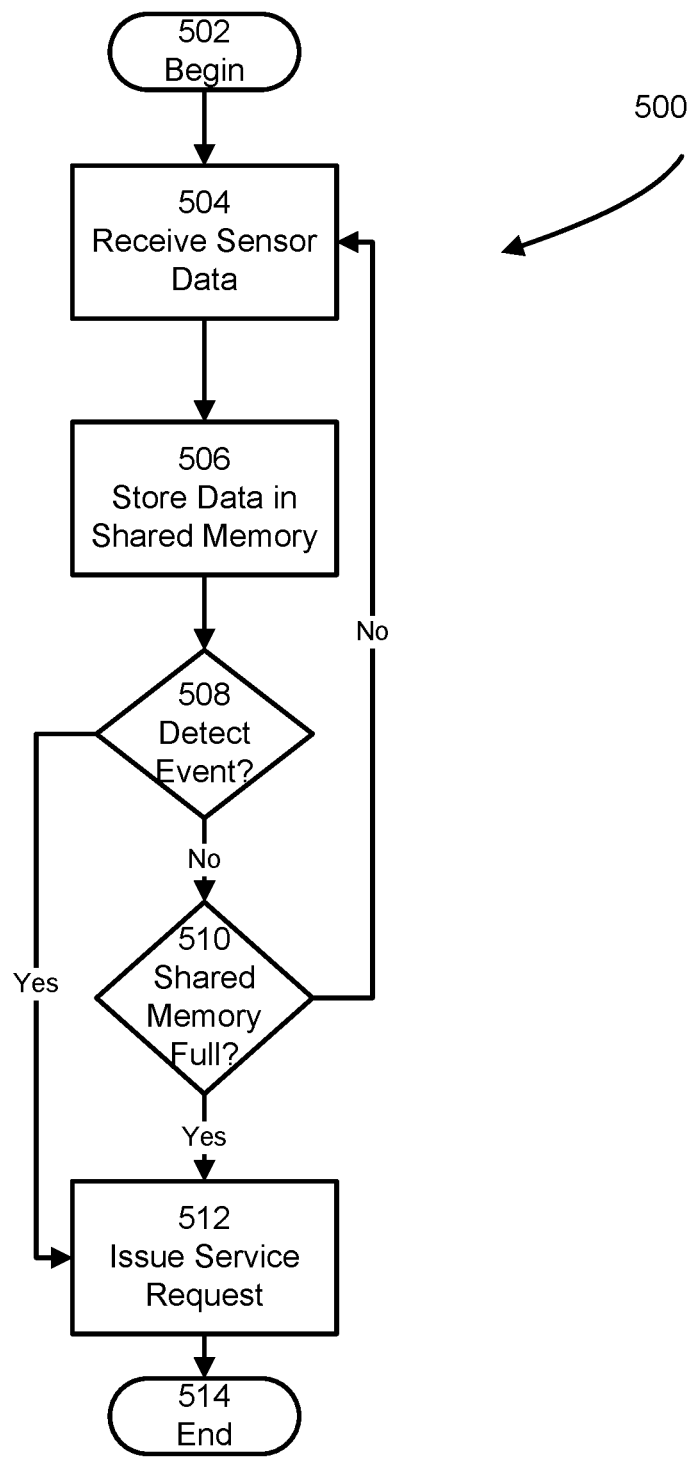
FIG. 5 is a flow diagram of one example of a method for monitoring critical functions of a medical device.

Process 400 ends at 410. Processes in accord with process 400 allow a medical device to perform its critical functions and to maintain a history of physiological data and events using components whose processing capabilities and power consumption are closely tailored to the tasks at hand. Thus, such processes allow the medical device to operate in an energy efficient manner As discussed above with regard to act 406 shown in FIG. 4, various examples provide processes for monitoring the critical functions of a medical device. FIG. 5 illustrates one such process 500 that may be used to implement act 406 and that includes acts of receiving sensor information, storing the sensor information in shared memory, detecting an event and issuing a request for service. A medical device implementing process 500 begins at 502.

In act 504, the critical purpose processor 104 of the medical device receives sensor data via the sensor interface 212. In act 506, the critical purpose processor 104 stores the sensor data in the shared memory 106. In act 508, the critical purpose processor analyzes information including the sensor data and determines whether a critical event has occurred. If a critical event was detected by the critical purpose processor 104, the critical purpose processor 104 proceeds to act 512 when the method for processing the critical event includes functionality that the general purpose processor 102 is configured to provide, such as interacting with a user through the user interface 208. Otherwise the critical purpose processor 104 proceeds to act 510. In act 510, the critical purpose processor 104 determines if the shared memory 106 is full or if a predetermined amount of time (e.g. 5 minutes) has passed since the critical purpose processor 104 last issued a service request to the general purpose processor 102. If the critical purpose processor 104 determines that either of these conditions is true, the critical purpose processor 104 proceeds to act 512, otherwise the critical purpose processor returns to act 504. In act 512, the critical purpose processor issues a service request to the general purpose processor 102. A medical device implementing process 500 terminates the process at 514.

Processes in accord with process 500 enable medical devices that utilize the power saving processor architecture disclosed herein to isolate critical functions to particular components of the medical device. In this way, such processes increase stable and efficient execution of critical functionality.

Figure 6:
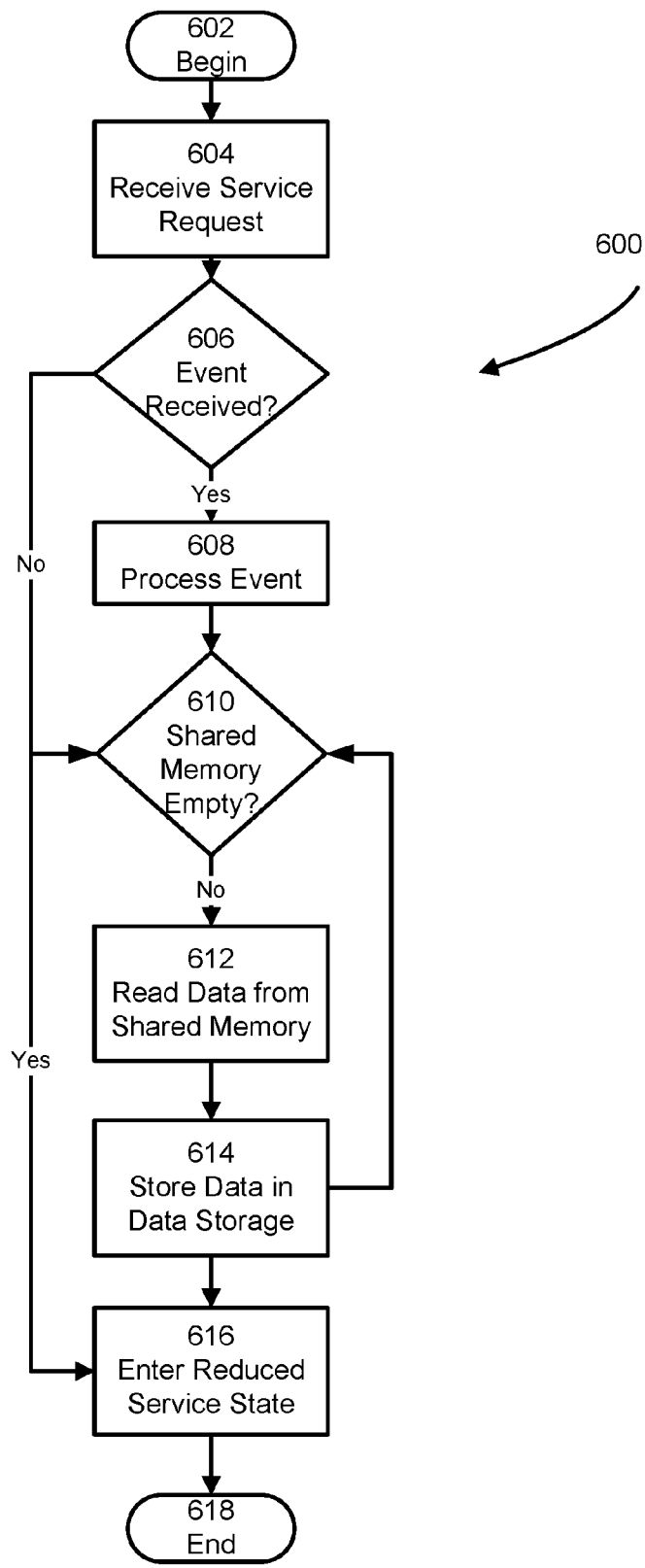
FIG. 6 is a flow diagram of one example of a method for processing a service request by made by a critical purpose processor.

As discussed above with regard to act 408 shown in FIG. 4, various examples provide processes for processing service requests in a medical device. FIG. 6 illustrates one such process 600 that may be used to implement act 408 and that includes acts of receiving a service request, reading data from shared memory, storing data in data storage, determining if the shared memory is empty, determining if a critical event was detected, processing critical events and entering a reduced service state. A medical device implementing process 600 begins at 602.

In act 604, the general purpose processor 102 receives a service request from the critical purpose processor 104. Upon receiving the service request, the general purpose processor 102 identifies a service state that provides the functionality required to process the service request and assumes the identified service state. In act 606, the general purpose processor 102 determines if a critical event was received from the critical purpose processor 104. If so, the general purpose processor 102 proceeds to act 608, which is discussed further below. Otherwise the general purpose processor 102 proceeds to act 610. In act 610, the general purpose processor 102 determines if the shared memory 106 is empty. If so, the general purpose processor 102 proceeds to act 616, otherwise the general purpose processor 102 proceeds to act 612. In act 612, the general purpose processor 102 reads data from the shared memory 106. In act 614, the general purpose processor 102 stores the data read in act 612 in the data storage 204 and returns to act 610. In act 616, after processing of the service request, the general purpose processor 102 enters a reduced service state to conserve power. A medical device implementing process 600 terminates the process at 618.

In act 608, the general purpose processor 102 performs a process that is responsive to the critical event received from the critical purpose processor 104. The particular acts included in the response process vary, depending upon the particular critical event received. For instance, in some examples, if the critical event is a cardiac dysrhythmia, the general purpose processor 102 conducts a responsiveness test to determine if the user should not have a therapeutic shock administered by the medical device and returns the results of the responsiveness test to the critical purpose processor 104. While conducting this responsiveness test, the general purpose processor 102 provides the user with 25 seconds to respond. In other examples, the general purpose processor 102 warns bystanders to step back and not interfere with the functioning of the device.

Processes in accord with process 600 enable medical devices that utilize the power conserving processor architecture disclosed herein while selectively leveraging the processing power of the general purpose processor 102. Thus, processes in accord with process 600 provide medical devices with a robust computing platform in a power efficient manner In these and other examples, the general purpose processor 102 performs many functions other than process 600 and examples are not limited to a particular set of processes or functions.

In addition, each of the processes disclosed herein depicts one particular sequence of acts in a particular example. The acts included in each of these processes may be performed by, or using, a medical device specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely a medical device configured according to the examples disclosed herein.

In general summary, examples and aspects of the disclosed herein include a power conserving processor and methods that conserve energy by distributing the execution of instructions across processors with different operating power requirements. While the bulk of the specification discusses this processor architecture in the context of a portable medical device, various aspects disclosed herein may be used in other contexts, such as non-portable medical devices or medical devices that treat abnormalities other than cardiac dysrhythmia. For instance, other abnormalities that may be treated using a portable medical device with a power conserving processor arrangement include epilepsy.

Having thus described several aspects of at least one example, it is to be appreciated various alterations, modifications, and improvements will readily occur to those skilled in the art. Such alterations, modifications, and improvements are intended to be part of this disclosure, and are intended to be within the scope of the examples disclosed herein. In addition, while many examples disclosed herein include two or more physically separate processors, other examples may be implemented on a single, multi-core processor with one core functioning as the critical purpose processor 102 and another core functioning as the general purpose processor 104. Other examples may employ three or more processors, each dedicated to a particular set of critical or non-critical functions. Accordingly, the foregoing description and drawings are by way of example only.

What is claimed is:

1. An external medical device comprising:
   at least one cardiac sensor to sense cardiac data of a patient;
   a shared memory; and
   a processor coupled to the shared memory and comprising a plurality of cores, the plurality of cores comprising:
   a digital signal processor core, coupled to the at least one cardiac sensor, and configured to receive cardiac data sensed by the at least one cardiac sensor; and
   a general purpose processor core configured to monitor a condition of the patient based on at least the cardiac data.

2. The external medical device of claim 1, further comprising a user interface coupled to the processor, wherein the general purpose processor core is configured to provide at least one notification via the user interface based on the condition of the patient.

3. The external medical device of claim 1, further comprising at least one treatment electrode coupled to the processor and configured to provide treatment to the patient.

4. The external medical device of claim 3, wherein the general purpose processor core is configured to adjust a treatment timeline of the patient.

5. The external medical device of claim 3, further comprising at least one response button coupled to the processor, wherein the general purpose processor core is configured to delay administration of treatment to the patient via the at least one treatment electrode responsive to actuation of the at least one response button.

6. The external medical device of claim 3, further comprising a motion sensor coupled to the processor, wherein the general purpose processor core is configured to accelerate administration of treatment to the patient via the at least one treatment electrode based on motion information sensed by the motion sensor.

7. The external medical device of claim 3, further comprising a motion sensor coupled to the processor, wherein the general purpose processor core is configured to delay administration of treatment to the patient via the at least one treatment electrode based on motion information sensed by the motion sensor.

8. The external medical device of claim 1, further comprising a communications device coupled to the processor, wherein the general purpose processor core is configured to communicate with an external system via the communications device.

9. The external medical device of claim 1, further comprising a node coupled between the at least one cardiac sensor and the digital signal processor core.

10. The external medical device of claim 9, wherein the node comprises at least one vibration device coupled to the general purpose processor core, wherein the general purpose processor core is configured to direct the at least one vibration device to vibrate based on the condition of the patient.

11. The external medical device of claim 9, wherein the node comprises a signal acquisition circuit to acquire the cardiac data sensed by the at least one cardiac sensor.

12. The external medical device of claim 1, wherein the general purpose processor core is configured to execute a real time operating system.

13. The external medical device of claim 1, wherein the digital signal processor core is configured to store the cardiac data in the shared memory.

14. The external medical device of claim 13, wherein the general purpose processor core is configured to retrieve the cardiac data from the shared memory and monitor the condition of the patient based on the retrieved cardiac data.

15. The external medical device of claim 1, wherein the at least one cardiac sensor comprises electrocardiographic electrodes.

16. The external medical device of claim 1, wherein the external medical device comprises a wearable defibrillator.

17. An external medical device comprising:
   at least one cardiac sensor to sense cardiac data of a patient;
   at least one treatment electrode;
   a user interface; and
   a processor coupled to the at least one cardiac sensor, the at least one treatment electrode, and the user interface device and being configured to monitor a condition of the patient based on the cardiac data and provide treatment to the patient via the at least one treatment electrode, the processor comprising a digital signal processor core configured to receive cardiac data sensed by the at least one cardiac sensor and a general purpose processor core configured to provide at least one notification via the user interface based on the condition of the patient.

18. The external medical device of claim 17, wherein the user interface comprises a display, wherein the general purpose processor core is configured to display the at least one notification via the display.

19. The external medical device of claim 17, wherein the user interface comprises a speaker, wherein the general purpose processor core is configured to provide an audible alarm via the speaker based on the condition of the patient.

20. The external medical device of claim 17, wherein the user interface comprises at least one vibration device, wherein the general purpose processor core is configured to direct the at least one vibration device to vibrate based on the condition of the patient.

21. The external medical device of claim 17, wherein the user interface comprises at least one response button, wherein the general purpose processor core is configured to delay administration of treatment to the patient via the at least one treatment electrode responsive to detecting actuation of the at least one response button.

22. The external medical device of claim 17, further comprising a motion sensor coupled to the processor to sense motion information, wherein the general purpose processor core is configured to accelerate administration of treatment to the patient via the at least one treatment electrode based on the motion information.

23. An external medical device comprising:
   a shared memory;
   a multi-core processor including a plurality of processor cores coupled to the shared memory, the plurality of processor cores including a general purpose processor core and a critical purpose processor core, the general purpose processor core being configured to process at least one event, and the critical purpose processor core being configured to:
   instruct the general purpose processor core to enter a reduced service state;
   detect at least one event that the general purpose processor core is configured to process; and
   instruct the general purpose processor core to enter an active state in which the general purpose processor core processes the at least one event.

* * * * *